(12) United States Patent
Schirok et al.

(10) Patent No.: US 8,114,400 B2
(45) Date of Patent: Feb. 14, 2012

(54) AZA-BICYCLIC COMPOUNDS AND THEIR USE AS STIMULATORS OF SOLUBLE GUANYLATE CYCLASE

(75) Inventors: Hartmut Schirok, Wuppertal (DE); Joachim Mittendorf, Wuppertal (DE); Johannes-Peter Stasch, Solingen (DE); Frank Wunder, Wuppertal (DE)

(73) Assignee: Bayer Pharma Aktiengesellschaft (DE)

( * ) Notice: Subject to any disclaimer, the term of this patent is extended or adjusted under 35 U.S.C. 154(b) by 264 days.

(21) Appl. No.: 12/515,211

(22) PCT Filed: Nov. 14, 2007

(86) PCT No.: PCT/EP2007/009827
§ 371 (c)(1),
(2), (4) Date: May 15, 2009

(87) PCT Pub. No.: WO2008/061657
PCT Pub. Date: May 29, 2008

(65) Prior Publication Data
US 2011/0038857 A1  Feb. 17, 2011

(30) Foreign Application Priority Data

Nov. 21, 2006  (DE) .................. 10 2006 054 757

(51) Int. Cl.
*A61K 39/395* (2006.01)
*A61K 31/53* (2006.01)
*A61K 33/08* (2006.01)
*A61K 31/60* (2006.01)
*C07D 251/00* (2006.01)
*A61P 9/10* (2006.01)
*A61P 9/12* (2006.01)
*A61P 9/00* (2006.01)

(52) U.S. Cl. ............... 424/133.1; 544/180; 514/241; 514/165; 424/718

(58) Field of Classification Search ............... None
See application file for complete search history.

(56) References Cited

U.S. PATENT DOCUMENTS

| | | | |
|---|---|---|---|
| 6,166,027 A | 12/2000 | Straub et al. | |
| 6,180,656 B1 | 1/2001 | Furstner et al. | |
| 6,451,805 B1 | 9/2002 | Straub et al. | |
| 6,903,089 B1 | 6/2005 | Stasch et al. | |
| 2002/0173514 A1 | 11/2002 | Stasch et al. | |
| 2004/0067937 A1 | 4/2004 | Stasch et al. | |
| 2004/0082596 A1 | 4/2004 | Stasch et al. | |
| 2004/0171832 A1 | 9/2004 | Stasch et al. | |
| 2004/0224945 A1 | 11/2004 | Straub et al. | |
| 2004/0235863 A1 | 11/2004 | Feurer et al. | |
| 2006/0052397 A1 | 3/2006 | Alonso-Alija et al. | |

FOREIGN PATENT DOCUMENTS

| | | |
|---|---|---|
| AU | 199951604 | 4/2000 |
| WO | WO-2005030121 | 4/2005 |

OTHER PUBLICATIONS

Schmidt et al. in the Handbook of Experimental Pharmacology 2009; (191):309-339.*
The National Heart and Lung Institute (www.nhlbi.nih.gov/health/dci/Diseases/Hf/HF_Prevention.html) (Jan. 1, 2010).*
Pettibone et al. in European Journal of Pharmacology, 116 (1985) 307-312.*
Feil et al. in EMBO reports (2006) 7, 149-153.*
A. Straub et al.: "NO-Independent Stimulators of Soluble Guanylate Cyclase," Bioorganic & Medicinal Chemistry Letters 11 (2000), pp. 781-784.
F-N Ko et al.: "YC-1, a Novel Activator of Platelet Guanylate Cyclase," Blood, vol. 84, No. 12, Dec. 15, 1994, pp. 4226-4233.
A. Mülsch et al.: "Effect of YC-1, an NO-Independent, Superoxide-Sensitive Stimulator of Soluble Guanylyl Cyclase, on Smooth Muscle Responsiveness to Nitrovasodilators," British Journal of Pharmacology, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.
D. J. Pettibone et al.: "A Structurally Novel Stimulator of Guanylate Cyclase with Long-Lasting Hypotensive Activity in the Dog," European Journal of Pharmacology, 116 (1985), pp. 307-312.
S-M. Yu et al.: "Vasorelaxant Effect of Isoliquiritigenin, a Novel Soluble Guanylate Cyclase Activator, in Rat Aorta," British Journal of Pharmacology, vol. 114 (1995), pp. 1587-1594.

* cited by examiner

*Primary Examiner* — Brandon Fetterolf
*Assistant Examiner* — Dennis Heyer
(74) *Attorney, Agent, or Firm* — Karen B. King

(57) ABSTRACT

The present application relates to novel azabicyclic compounds, processes for their preparation, their use alone or in combinations for the treatment and/or prevention of diseases, and their use for producing medicaments for the treatment and/or prevention of diseases, especially for the treatment and/or prevention of cardiovascular disorders.

5 Claims, No Drawings

AZA-BICYCLIC COMPOUNDS AND THEIR USE AS STIMULATORS OF SOLUBLE GUANYLATE CYCLASE

RELATED APPLICATIONS/PATENTS AND INCORPORATION BY REFERENCE

This application is a National Stage Application filed under 35 U.S.C. §371 based on International Application No. PCT/EP2007/009827, filed Nov. 14, 2007, which claims priority to German Patent Application Number 102006054757.8, filed Nov. 21, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel azabicyclic compounds, processes for their preparation, their use alone or in combinations for the treatment and/or prevention of diseases, and their use for producing medicaments for the treatment and/or prevention of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

Fused pyrazole derivatives are described inter alia in WO 98/16507, WO 98/23619, WO 00/06567, WO 00/06569, WO 02/42299, WO 02/42300, WO 02/42301, WO 02/42302, WO 02/092596, WO 03/004503 and WO 03/095451 as stimulators of soluble guanylate cyclase. However, it has emerged that these compounds sometimes display disadvantages in terms of their physicochemical properties such as, for example, their solubility, or in relation to their in vivo properties, such as, for example, their behavior in the liver, their pharmacokinetic behavior, their dose-effect relation and/or their metabolic pathway.

In addition, WO 2005/030121 claims fused azoles for the treatment of neoplastic diseases.

It was an object of the present invention to provide novel substances which act as stimulators of soluble guanylate cyclase and display an improved therapeutic profile by comparison with compounds known in the prior art.

The present invention relates to compounds of the general formula (I)

in which

L is phenyl, pyridyl, furyl, thienyl, thiazolyl, oxazolyl, isothiazolyl or isoxazolyl, each of which may be substituted up to twice, identically or differently, by halogen, cyano, $(C_1-C_4)$-alkyl, trifluoromethyl and/or $(C_2-C_4)$-alkynyl, or is $(C_5-C_7)$-cycloalkyl which may be substituted up to twice, identically or differently, by fluorine and/or $(C_1-C_4)$-alkyl, M is a bicyclic heteroaryl group having one of the formulae (a) to (i)

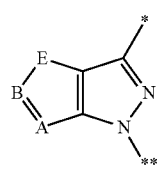

(a)

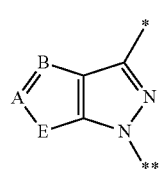

(b)

(c)
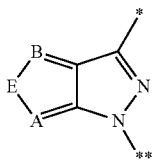

(d)
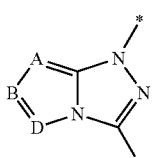

(e)
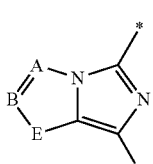

(f)
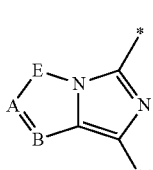

(g)
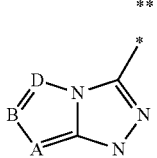

(h)
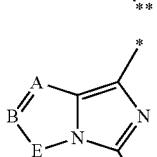

(i)
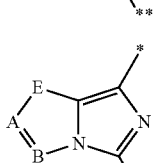

in which

* is the point of linkage to the —CH$_2$-L group,
** is the point of linkage to the Q group,
A, B and D are each CH, CR$^1$ or N, with a maximum of two of the ring members A, B and D simultaneously being N and in which
R$^1$ is a substituent selected from the series halogen, cyano, (C$_1$-C$_4$)-alkyl, trifluoro-methyl, amino, (C$_1$-C$_4$)-alkoxy and trifluoromethoxy,
where, in the event that the substituent R$^1$ occurs more than once, its meanings may be identical or different,
and
E is O or S,
and
Q is an unsaturated or aromatic 5- or 6-membered heterocycle having up to four heteroatoms from the series N, O and/or S, which may be substituted up to four times, identically or differently, by radicals selected from the group consisting of halogen, azido, nitro, cyano, oxo, thioxo, —R$^2$, —C(=O)—R$^2$, —C(=O)—OR$^2$, —C(=O)—NR$^2$R$^3$, —O—(C=O)$_n$—R$^2$, —O—C(=O)—OR$^2$, —O—C(=O)—NR$^2$R$^3$, —S(O)$_p$—R$^2$, —SO$_2$—OR$^2$, —SO$_2$—NR$^2$R$^3$, —NR$^2$—(C=O)$_n$—R$^3$, —NR$^2$—SO$_2$—R$^3$, —NR$^2$—C(=O)—OR$^3$, —NR$^4$—C(=O)—NR$^2$R$^3$ and —NR$^4$—SO$_2$—NR$^2$R$^3$, in which n is the number 0 or 1,
p is the number 0, 1 or 2,
R$^2$, R$^3$ and R$^4$ are identical or different and are independently of one another hydrogen, (C$_1$-C$_6$)-alkyl, (C$_2$-C$_6$)-alkenyl, (C$_3$-C$_8$)-cycloalkyl, (C$_3$-C$_8$)-cycloalkenyl, (C$_6$-C$_{10}$)-aryl, 4- to 8-membered heterocyclyl or 5- to 10-membered heteroaryl,
and/or
R$^2$ and R$^3$ or R$^2$ and R$^4$ together with the radical to which they are both respectively bonded may form a 4- to 8-membered heterocycle,
where R$^2$, R$^3$ and R$^4$ in turn may optionally be substituted up to five times, identically or differently, by radicals selected from the group consisting of halogen, azido, nitro, cyano, (C$_1$-C$_6$)-alkyl, trifluoromethyl, (C$_1$-C$_6$)-acyl, hydroxycarbonyl, (C$_1$-C$_6$)-alkoxycarbonyl, aminocarbonyl, mono- and di-(C$_1$-C$_6$)-alkylaminocarbonyl, hydroxy, (C$_1$-C$_6$)-alkoxy, trifluoromethoxy, (C$_1$-C$_6$)-acyloxy, oxo, mercapto, (C$_1$-C$_6$)-alkylthio, amino, mono- and di-(C$_1$-C$_6$)-alkylamino, (C$_1$-C$_6$)-acylamino, (C$_1$-C$_6$)-alkoxycarbonylamino, (C$_3$-C$_8$)-cycloalkyl, (C$_3$-C$_8$)-cycloalkenyl and 4- to 8-membered heterocyclyl, and the N-oxides, salts, solvates, salts of the N-oxides and solvates of the N-oxides and salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

Compounds according to the invention are likewise N-oxides of the compounds of the formula (I), and the salts, solvates and solvates of the salts thereof.

The compounds according to the invention may, depending on their structure, exist in stereoisomeric forms (enantiomers, diastereomers). The present invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_2-C_6)$-Alkenyl and $(C_2-C_4)$-alkenyl are in the context of the invention a straight-chain or branched alkenyl radical having respectively 2 to 6 and 2 to 4 carbon atoms and one or two double bonds. A straight-chain or branched alkenyl radical having 2 to 4 carbon atoms and one double bond is preferred. Examples which may be preferably mentioned are: vinyl, allyl, isopropenyl and n-but-2-en-1-yl.

$(C_2-C_4)$-Alkynyl is in the context of the invention a straight-chain or branched alkynyl radical having 2 to 4 carbon atoms and a triple bond. A straight-chain alkynyl radical having 2 to 4 carbon atoms is preferred. Examples which may be preferably mentioned are: ethynyl, n-prop-1-yn-1-yl, n-prop-2-yn-1-yl, n-but-1-yn-1-yl, n-but-2-yn-1-yl and n-but-3-yn-1-yl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

$(C_1-C_6)$-Alkylthio and $(C_1-C_4)$-alkylthio are in the context of the invention a straight-chain or branched alkylthio radical having respectively 1 to 6 and 1 to 4 carbon atoms. A straight-chain or branched alkylthio radical having 1 to 4 carbon atoms is preferred. Examples which may be preferably mentioned are: methylthio, ethylthio, n-propylthio, isopropylthio, n-butylthio, tert-butylthio, n-pentylthio and n-hexylthio.

Mono-$(C_1-C_6)$-alkylamino and mono-$(C_1-C_4)$-alkylamino are in the context of the invention an amino group having one straight-chain or branched alkyl substituent which has respectively 1 to 6 and 1 to 4 carbon atoms. A straight-chain or branched monoalkylamino radical having 1 to 4 carbon atoms is preferred. Examples which may be preferably mentioned are: methylamino, ethylamino, n-propylamino, isopropylamino, n-butylamino, tert-butylamino, n-pentylamino and n-hexylamino Di-$(C_1-C_6)$-alkylamino and di-$(C_1-C_4)$-alkylamino are in the context of the invention an amino group having two identical or different straight-chain or branched alkyl substituents each having respectively 1 to 6 and 1 to 4 carbon atoms. Straight-chain or branched dialkylamino radicals each having 1 to 4 carbon atoms are preferred. Examples which may be preferably mentioned are: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

$(C_1-C_6)$-Acyl and $(C_1-C_4)$-acyl [$(C_1-C_6)$-alkanoyl and $(C_1-C_4)$-alkanoyl] are in the context of the invention a straight-chain or branched alkyl radical having respectively 1 to 6 and 1 to 4 carbon atoms which has a doubly bonded oxygen atom in position 1 and is linked via position 1. An acyl radical having 1 to 4 carbon atoms is preferred. Examples which may be preferably mentioned are: formyl, acetyl, propionyl, n-butyryl, iso-butyryl, n-pentanoyl, pivaloyl and n-hexanoyl.

$(C_1-C_6)$-Acylamino and $(C_1-C_4)$-acylamino are in the context of the invention an amino group having one straight-chain or branched acyl substituent which has respectively 1 to 6 and 1 to 4 carbon atoms and is linked via the carbonyl group to the N atom. Examples which may be preferably mentioned are: formylamino, acetylamino, propionylamino, n-butyrylamino, iso-butyrylamino and pivaloylamino.

$(C_1-C_6)$-Acyloxy and $(C_1-C_4)$-acyloxy are in the context of the invention a straight-chain or branched alkyl radical having respectively 1 to 6 and 1 to 4 carbon atoms which has a doubly bonded oxygen atom in position 1 and is linked via a further oxygen atom in position 1. Examples which may be preferably mentioned are: acetoxy, propionoxy, n-butyroxy, iso-butyroxy and pivaloyloxy.

$(C_1-C_6)$-Alkoxycarbonyl and $(C_1-C_4)$-alkoxycarbonyl are in the context of the invention a straight-chain or branched alkoxy radical having respectively 1 to 6 and 1 to 4 carbon atoms which is linked via a carbonyl group. A straight-chain or branched alkoxycarbonyl radical having 1 to 4 carbon atoms in the alkoxy group is preferred. Examples which may be preferably mentioned are: methoxycarbonyl, ethoxycarbonyl, n-propoxycarbonyl, isopropoxycarbonyl, n-butoxycarbonyl and tert-butoxycarbonyl.

$(C_1-C_6)$-Alkoxycarbonylamino and $(C_1-C_4)$-alkoxycarbonylamino are in the context of the invention an amino group having one straight-chain or branched alkoxycarbonyl substituent which has respectively 1 to 6 and 1 to 4 carbon atoms and is linked via the carbonyl group to the N atom. Examples which may be preferably mentioned are: methoxycarbonylamino, ethoxycarbonylamino, n-propoxycarbonylamino, isopropoxycarbonylamino, n-butoxycarbonylamino and tert-butoxy-carbonylamino.

Mono- or di-$(C_1-C_6)$-alkylaminocarbonyl and mono- or di-$(C_1-C_4)$-alkylaminocarbonyl are in the context of the invention an amino group which is linked via a carbonyl group and which has one straight-chain or branched, or two identical or different straight-chain or branched, alkyl substituents each having respectively 1 to 6 and 1 to 4 carbon atoms. A mono- or dialkylaminocarbonyl radical having 1 to 4 carbon atoms in the alkyl group is preferred. Examples which may preferably be mentioned are: methylaminocarbonyl, ethylaminocarbonyl, n-propylaminocarbonyl, isopropylaminocarbonyl, n-butylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

$(C_3-C_8)$-Cycloalkyl, $(C_3-C_7)$-cycloalkyl, $(C_3-C_6)$-cycloalkyl and $(C_5-C_7)$-cycloalkyl are in the context of the invention a monocyclic, saturated carbocycle having respectively 3 to 8, 3 to 7, 3 to 6 and 5 to 7 ring carbon atoms. Examples which may be preferably mentioned are: cyclopropyl, cyclobutyl, cyclopentyl, cyclohexyl, cycloheptyl and cyclooctyl.

$(C_3-C_8)$-Cycloalkenyl and $(C_3-C_7)$-cycloalkenyl are in the context of the invention a monocyclic carbocycle having respectively 3 to 8 and 3 to 7 ring carbon atoms and one double bond. Examples which may be preferably mentioned are: cyclobutenyl, cyclopentenyl, cyclohexenyl, cycloheptenyl and cyclooctenyl.

$(C_6-C_{10})$-Aryl is in the context of the invention an aromatic carbocycle having 6 or 10 ring carbon atoms. Preferred aryl radicals are phenyl and naphthyl.

5- to 10-membereed heteroaryl is in the context of the invention a mono- or, where appropriate, bicyclic aromatic heterocycle (heteroaromatic) having a total of 5 to 10 ring atoms which comprises up to three identical or different ring heteroatoms from the series N, O and/or S and is linked via a ring carbon atom or, where appropriate, via a ring nitrogen atom. Examples which may be mentioned are: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Monocyclic 5- or 6-membered heteroaryl radicals having up to three ring heteroatoms from the series N, O and/or S are preferred, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

A 4- to 8-membered heterocycle is in the context of the invention a monocyclic, saturated heterocycle having a total of 4 to 8 ring atoms which comprises one or two ring heteroatoms from the series N, O, S, SO and/or $SO_2$ and is linked via a ring carbon atom or, where appropriate, a ring nitrogen atom. A 5- to 7-membered heterocycle having one or two ring heteroatoms from the series N, O and/or S is preferred, and a 5- or 6-membered heterocycle having one or two ring heteroatoms from the series N and/or O is particularly preferred. Examples which may be mentioned are: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Pyrrolidinyl, tetrahydrofuranyl, piperidinyl, piperazinyl, tetrahydropyranyl and morpholinyl are preferred.

An unsaturated or aromatic 5- or 6-membered heterocycle is in the context of the invention a monocyclic heterocycle having a total of 5 or 6 ring atoms which comprises up to four ring heteroatoms from the series N, O and/or S, is linked via a ring carbon atom or, where appropriate, a ring nitrogen atom, and in the case of the five-membered ring contains a double bond or is aromatic, and in the case of the 6-membered ring contains one or two double bonds or is aromatic. Examples which may be mentioned are: pyrrolinyl, dihydropyrazolyl, imidazolinyl, dihydrooxazolyl, dihydroisoxazolyl, dihydro-1,2,4-triazolyl, dihydro-1,2,4-oxadiazolyl, dihydro-1,3,4-oxadiazolyl, dihydro-1,2,4-thiadiazolyl, dihydropyranyl, 1,4-dihydropyridyl, tetrahydropyrimidinyl, 1,3-oxazinyl, furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl, triazinyl.

Halogen in the context of the invention includes fluorine, chlorine, bromine and iodine. Fluorine or chlorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which L is phenyl or thienyl, each of which may be substituted up to twice, identically or differently, by fluorine, chlorine, cyano, methyl and/or trifluoromethyl, or is cyclohexyl or cycloheptyl, each of which may be substituted up to twice, identically or differently, by fluorine and/or methyl, M is a bicyclic heteroaryl group of the formula (b), (d), (e) or (h)

(b)

(d)

(e)

(h)

in which
* is the point of linkage to the —CH$_2$-L group,
** is the point of linkage to the Q group,
A, B and D are each CH, CR$^1$ or N, with a maximum of two of the ring members A, B and D simultaneously being N and in which
R$^1$ is a substituent selected from the series fluorine, chlorine, bromine, cyano, (C$_1$-C$_4$)-alkyl, trifluoromethyl, amino, (C$_1$-C$_4$)-alkoxy and trifluoromethoxy,
where, in the event that the substituent R$^1$ occurs more than once, its meanings may be identical or different,
and
E is O or S,
and
Q is a group of the formula

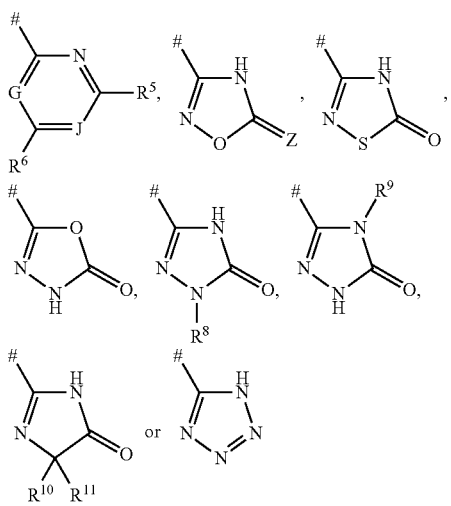

in which
# is the point of linkage to the M group,
G is CH or N,
J is CR$^7$ or N,
Z is O or S,
R$^5$, R$^6$ and R$^7$ are identical or different and are independently of one another a radical selected from the group consisting of halogen, nitro, cyano, —R$^2$, —C(=O)—R$^2$, —C(=O)—OR$^2$, —C(=O)—NR$^2$R$^3$, —O—(C=O)$_n$—R$^2$, —O—C(=O)—OR$^2$, —O—C(=O)—NR$^2$R$^3$, —S(O)$_p$—R$^2$, —SO$_2$—OR$^2$, —SO$_2$—NR$^2$R$^3$, —NR$^2$—(C=O)$_n$—R$^3$, —NR$^2$—SO$_2$—R$^3$, —NR$^2$—C(=O)—OR$^3$, —NR$^4$—C(=O)—NR$^2$R$^3$ and —NR$^4$—SO$_2$—NR$^2$R$^3$, in which
n is the number 0 or 1,
p is the number 0 or 2,
R$^2$, R$^3$ and R$^4$ are identical or different and are independently of one another hydrogen, (C$_1$-C$_6$)-alkyl, (C$_2$-C$_6$)-alkenyl, (C$_3$-C$_7$)-cycloalkyl, (C$_3$-C$_7$)-cycloalkenyl, phenyl, 5- to 7-membered heterocyclyl or 5- or 6-membered heteroaryl,
and/or
R$^2$ and R$^3$ or R$^2$ and R$^4$ together with the radical to which they are both respectively bonded may form a 5- to 7-membered heterocycle,
where R$^2$, R$^3$ and R$^4$ in turn may optionally be substituted up to three times, identically or differently, by radicals selected from the group consisting of fluorine, chlorine, cyano, (C$_1$-C$_4$)-alkyl, trifluoromethyl, hydroxy, (C$_1$-C$_4$)-alkoxy, trifluoromethoxy, oxo, amino, mono-(C$_1$-C$_4$)-alkylamino and di-(C$_1$-C$_4$)-alkylamino,
R$^8$ is hydrogen, (C$_1$-C$_6$)-alkyl or (C$_3$-C$_7$)-cycloalkyl,
where (C$_1$-C$_6$)-alkyl may be substituted up to five times by fluorine and up to twice, identically or differently, by (C$_3$-C$_7$)-cycloalkyl, hydroxy, (C$_1$-C$_4$)-alkoxy, trifluoromethoxy, (C$_1$-C$_4$)-acyloxy, amino, mono-(C$_1$-C$_4$)-alkylamino, di-(C$_1$-C$_4$)-alkylamino, (C$_1$-C$_4$)-acylamino, hydroxycarbonyl, (C$_1$-C$_4$)-alkoxycarbonyl, aminocarbonyl, mono-(C$_1$-C$_4$)-aminocarbonyl, di-(C$_1$-C$_4$)-alkylaminocarbonyl and/or a 5- or 6-membered heterocycle,
R$^9$ is (C$_1$-C$_4$)-alkyl which may be substituted by hydroxy, (C$_1$-C$_4$)-alkoxy, amino, mono-(C$_1$-C$_4$)-alkylamino, di-(C$_1$-C$_4$)-alkylamino or up to three times by fluorine,
R$^{10}$ has the meaning indicated above for R$^8$,
and
R$^{11}$ is hydrogen or (C$_1$-C$_4$)-alkyl,
and the N-oxides, salts, solvates, salts of the N-oxides and solvates of the N-oxides and salts thereof.

Particular preference is given in the context of the present invention to compounds of the formula (I) in which
L is phenyl which may be substituted up to twice by fluorine,
M is a bicyclic heteroaryl group of the formula

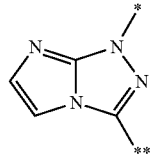

in which
* is the point of linkage to the —CH$_2$-L group
and
** is the point of linkage to the Q group,
and
Q is a group of the formula

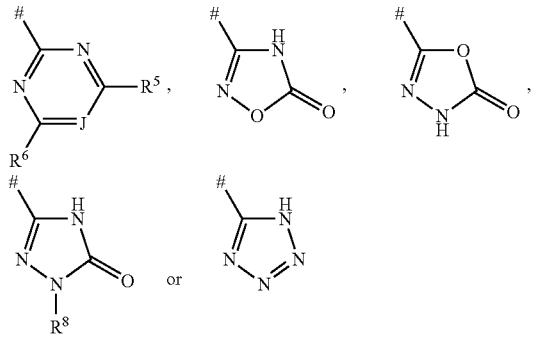

in which
# is the point of linkage to the M group,
J is CR$^7$ or N,
R$^5$ and R$^6$ are independently of one another hydrogen or amino,
R$^7$ is hydrogen, fluorine, chlorine, bromine, (C$_1$-C$_4$)-alkyl, (C$_3$-C$_6$)-cycloalkyl, pyridyl or —NR$^{12}$R$^{13}$, in which
R$^{12}$ is hydrogen or (C$_1$-C$_4$)-alkyl which may be substituted by hydroxy, methoxy or up to three times by fluorine, $R^{13}$ is hydrogen, $(C_1-C_4)$-alkyl which may be substituted by hydroxy, methoxy or up to three times by fluorine, or $(C_1-C_4)$-acyl, $(C_1-C_4)$-alkoxycarbonyl or mono- or di-$(C_1-C_4)$-alkylaminocarbonyl, or $R^{12}$ and $R^{13}$ together with the nitrogen atom to which they are bonded form a 5- to 7-membered heterocycle which may be substituted by oxo, and $R^8$ is hydrogen or $(C_1-C_4)$-alkyl which may be substituted up to three times by fluorine, and the N-oxides, salts, solvates, salts of the N-oxides and solvates of the N-oxides and salts thereof.

The definitions of radicals indicated specifically in their respective combinations or preferred combinations of radicals are replaced as desired irrespective of the particular combinations indicated for the radicals also by definitions of radicals of other combinations.

Combinations of two or more of the abovementioned preferred ranges are particularly preferred.

Very particular preference is given to the compound 6-[1-(2-fluorobenzyl)-1H-imidazo[2,1-c][1,2,4]triazol-3-yl]-1,3,5-triazin-2,4-diamine and the N-oxides, salts, solvates, salts of the N-oxides and solvates of the N-oxides and salts thereof.

The compounds of the invention of the formula (I) can be prepared in analogy to methods described in the literature for example by

[A] Condensing a Compound of the Formula (II)

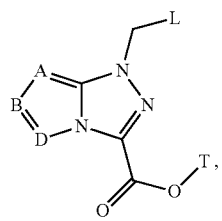

(II)

in which A, B, D and L each have the meanings indicated above, and

T is $(C_1-C_4)$-alkyl, with a compound of the formula (III)

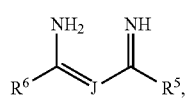

(III)

in which J, $R^5$ and $R^6$ each have the meanings indicated above, to give a compound of the formula (I-A)

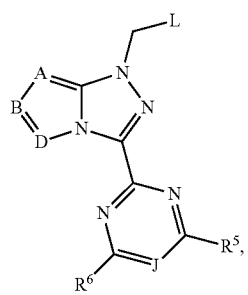

(I-A)

in which A, B, D, J, L, $R^5$ and $R^6$ each have the meanings indicated above, or

[B] Reacting a Compound of the Formula (IV)

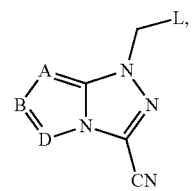

(IV)

in which A, B, D and L each have the meanings indicated above, with a compound of the formula (V)

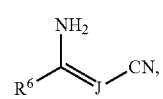

(V)

in which J and $R^6$ have the meanings indicated above, to give a compound of the formula (I-B)

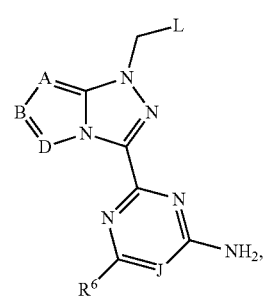

(I-B)

in which A, B, D, J, L and $R^6$ each have the meanings indicated above, or

[C] Converting a Compound of the Formula (VI)

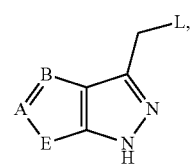

(VI)

in which A, B, E and L each have the meanings indicated above, with a compound of the formula (VII)

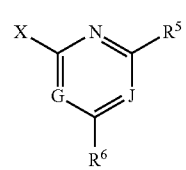

(VII)

in which G, J, $R^5$ and $R^6$ each have the meanings indicated above, and

X is a suitable leaving group such as, for example, halogen, mesylate, tosylate or triflate, into a compound of the formula (I-C)

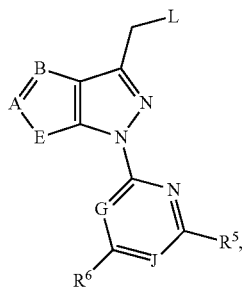
(I-C)

in which A, B, E, G, J, L, $R^5$ and $R^6$ each have the meanings indicated above, or

[D] Reacting a Compound of the Formula (VIII)

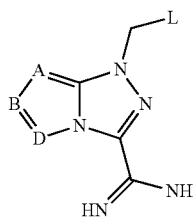
(VIII)

in which A, B, D and L each have the meanings indicated above, with a compound of the formula (IXa), (IXb), (IXc) or (IXd)

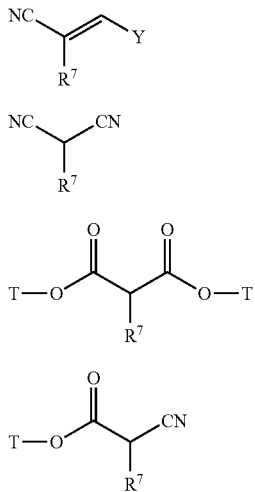
(IXa)
(IXb)
(IXc)
(IXd)

in which $R^7$ and T have the meanings indicated previously, and

Y is amino, mono- or di-$(C_1-C_4)$-alkylamino, piperidino, morpholino, hydroxy, $(C_1-C_4)$-alkoxy or $(C_1-C_4)$-acyloxy, to give a compound of the formula (I-D), (I-E), (I-F) or (I-G)

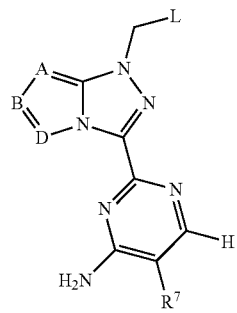
(I-D)

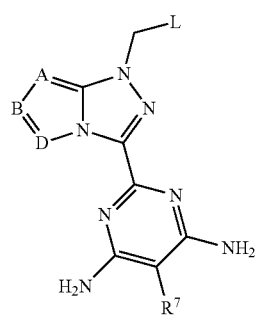
(I-E)

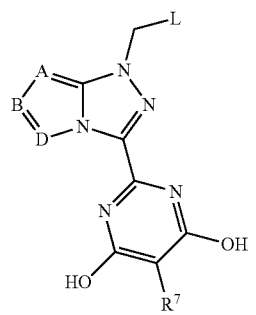
(I-F)

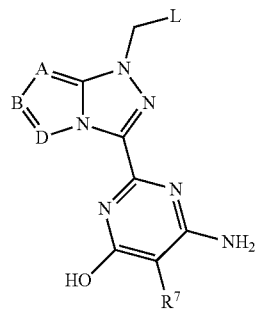
(I-G)

in which A, B, D, L and $R^7$ each have the meanings indicated above, or

[E] Converting a Compound of the Formula (IV)

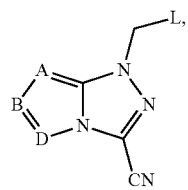
(IV)

in which A, B, D and L each have the meanings indicated above,
with an alkali metal azide in the presence of an acid or with trimethylsilyl azide in the presence of a catalyst such as dibutyltin oxide into a compound of the formula (I-H)

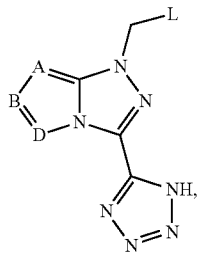
(I-H)

in which A, B, D and L each have the meanings indicated above,
or
[F] Firstly Converting a Compound of the Formula (IV)

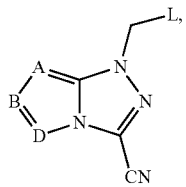
(IV)

in which A, B, D and L each have the meanings indicated above,
with hydroxylamine into a compound of the formula (X)

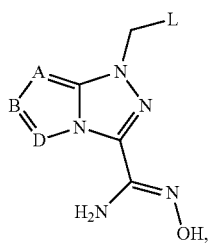
(X)

in which A, B, D and L each have the meanings indicated above, and then reacting the latter with phosgene or a phosgene equivalent such as N,N'-carbonyl-diimidazole or a chloroformate to give a compound of the formula (I-J)

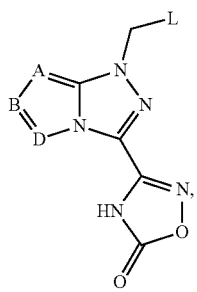
(I-J)

in which A, B, D and L each have the meanings indicated above,
or
[G] Firstly Converting a Compound of the Formula (II)

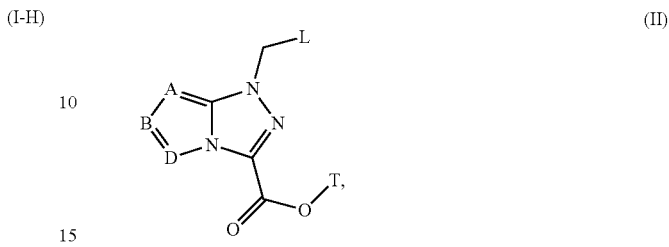
(II)

in which A, B, D, L and T each have the meanings indicated above,
with hydrazide into a compound of the formula (XI)

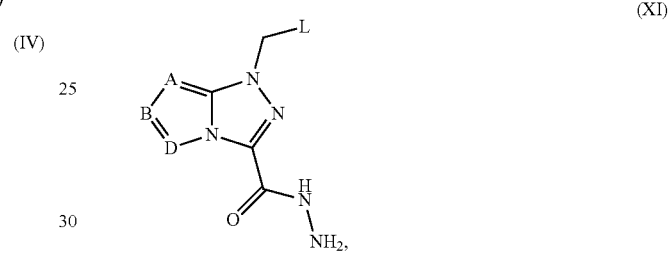
(XI)

in which A, B, D and L each have the meanings indicated above,
and then reacting the latter with phosgene or a phosgene equivalent such as N,N'-carbonyl-diimidazole or a chloroformate to give a compound of the formula (I-K)

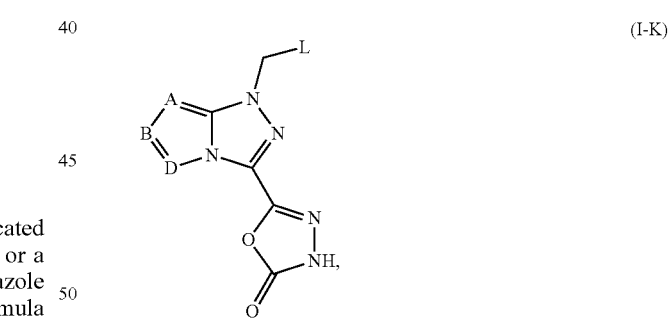
(I-K)

in which A, B, D, and L each have the meanings indicated above,
where appropriate modifying the resulting compounds of the formulae (I-A), (I-B), (I-C), (I-D), (I-E), (I-F), (I-G), (I-H), (I-J) and (I-K) by processes customary in the literature further in the scope indicated above of the meanings of the individual substituents and radicals,
and converting the compounds of the invention obtained in this way where appropriate with the appropriate (i) solvents and/or (ii) acids or bases into the solvates, salts and/or solvates of the salts thereof.

The compounds of the formulae (II), (IV), (VI) and (VIII) can be prepared in analogy to methods known from the literature starting from compounds which are commercially available or described in the literature (cf. reaction schemes 1-7 below). The compounds of the formulae (III), (V), (VII),

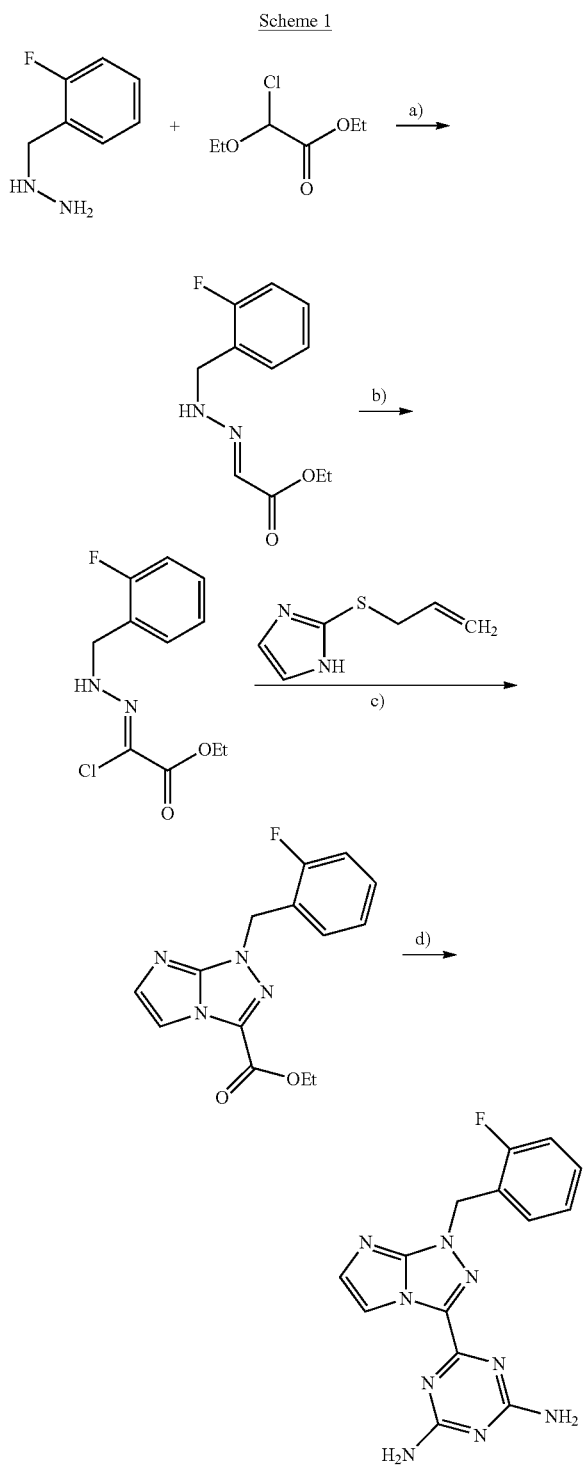

[a): water/dioxane, RT; b) N-chlorosuccinimide, ethyl acetate, 60° C.; c): triethylamine, dioxane, 100° C.; d) biguanidine dihydrochloride, sodium methoxide, methanol, 65° C.].

(IXa), (IXb), (IXc) and (IXd) are commercially available, known from the literature or can be prepared by methods customary in the literature.

The preparation of the compounds of the invention can be illustrated by way of example by the following synthesis scheme:

The compounds of the invention have valuable pharmacological properties and can be used for the prevention and treatment of disorders in humans and animals. The compounds of the invention open up a further treatment alternative and represent an enrichment of pharmacy.

The compounds of the invention have a vasorelaxant and platelet aggregation-inhibiting effect and lead to a reduction in blood pressure and to an increase in the coronary blood flow. These effects are mediated by a direct stimulation of soluble guanylate cyclase and an intracellular increase in cGMP.

In addition, the compounds of the invention enhance the effect of substances which increase the cGMP level, such as, for example, EDRF (endothelium-derived relaxing factor), NO donors, protoporphyrin IX, arachidonic acid or phenylhydrazine derivatives.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, reperfusion damage, for the prevention of restenoses as after thrombolysis therapies, percutaneous transluminal angioplasties (PTA), percutaneous transluminal coronary angioplasties (PTCA) and bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders, and for promoting wound healing.

The compounds according to the invention are furthermore suitable for the treatment of acute and chronic pulmonary diseases such as respiratory distress syndromes (ALI, ARDS) and chronic obstructive airway disorders (COPD), and for treating acute and chronic renal failure.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occuring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disorders, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:
  organic nitrates and NO donors such as, for example, sodium nitroprusside, nitroglycerin, isosorbide mononitrate, isosorbide dinitrate, molsidomine or SIN-1, and inhaled NO;
  compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
  agents having antithrombotic activity, for example and preferably from the group of platelet aggregation inhibitors, of anticoagulants or of profibrinolytic substances;
  active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
  active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidine or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, CholestaGel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays, tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms aq. aqueous solution
calc. calculated
conc. concentrated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high pressure, high performance liquid chromatography
HRMS high resolution mass spectrometry
LC/MS coupled liquid chromatography-mass spectrometry
min minute(s)
MS mass spectrometry
NMR nuclear magnetic resonance spectrometry
RT room temperature
$R_t$ retention time (in HPLC)
THF tetrahydrofuran
UV ultraviolet spectrometry
v/v volume to volume ratio (of a solution)
LC/MS Methods:
Method 1 (LC/MS):

MS instrument type: Micromass ZQ; HPLC instrument type: HP 1100 Series; UV DAD; column: Phenomenex Gemini 3µ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 2 (LC/MS):

MS instrument type: Micromass ZQ; HPLC instrument type: Waters Alliance 2795; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 3 (LC/MS):

Instrument: Micromass Quattro LCZ with HPLC Agilent Series 1100; column: Phenomenex Onyx Monolithic C18, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow rate: 2 ml/min; oven: 40° C.; UV detection: 208-400 nm.

Starting Compounds and Intermediates

Example 1A

Ethyl (2E)-[(2-fluorobenzyl)hydrazono]acetate

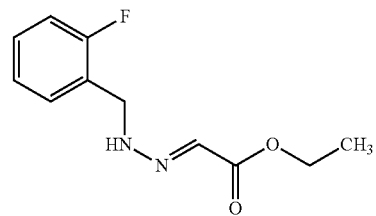

(2-Fluorobenzyl)hydrazine (1.00 g, 7.14 mmol) is suspended in water (3 ml), and the mixture is brought to pH 4 with 4N hydrochloric acid. It is then cooled in an ice bath, and a solution of ethyl chloro(ethoxy)acetate (1.37 g, 8.21 mmol) in dioxane (10 ml) is added. The mixture is stirred at RT for 1 h, then made weakly alkaline (pH 8) with 1N sodium hydroxide solution and extracted with ethyl acetate. The organic phase is dried over sodium sulfate. The crude product is purified by chromatography on silica gel (eluent: dichloromethane with increasing methanol content). 1.40 g (88% of theory) of the desired compound are obtained.

$^1$H-NMR (400 MHz, DMSO-d$_6$): δ=1.19 (t, J=7.1 Hz, 3H), 4.09 (q, J=7.1 Hz, 2H), 4.42 (d, J=4.4 Hz, 2H), 6.74 (s, 1H), 7.18-7.24 (m, 2H), 7.31-7.40 (m, 2H), 9.18 (t, J=4.4 Hz, 1H).

$^{13}$C-NMR (125 MHz, DMSO-d$_6$): δ=14.2, 44.2 (br), 59.2, 115.3 (d, $^2J_{C,F}$=21.1 Hz), 119.3 (br), 123.2 (br), 124.4 (d, $^4J_{C,F}$=3.4 Hz), 129.6 (d, $^3J_{C,F}$=8.2 Hz), 130.2 (d, $^3J_{C,F}$=4.2 Hz), 160.2 (d, $^1J_{C,F}$=245 Hz), 164.1.

HRMS: calc. for $C_{11}H_{13}FN_2O_2$ 224.0961; found 224.0962.

LC/MS (Method 2): $R_t$=1.83 min; MS (ESIpos): m/z=225 [M+H]$^+$.

Example 2A

Ethyl (2Z)-chloro[(2-fluorobenzyl)hydrazono]acetate

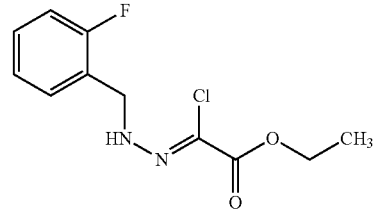

Ethyl (2E)-[(2-fluorobenzyl)hydrazono]acetate (300 mg, 1.14 mmol) from example 1A are dissolved in ethyl acetate (2.0 ml). N-Chlorosuccinimide (143 mg, 1.07 mmol) is added, and the mixture is stirred at 60° C. for 1 h. It is then concentrated in vacuo, and the residue is stirred with carbon tetrachloride. The filtrate after filtration is concentrated. 292 mg (82% of theory) of the desired compound are obtained.

$^1$H-NMR (400 MHz, DMSO-d$_6$): δ=1.22 (t, J=7.1 Hz, 3H), 4.19 (q, J=7.1 Hz, 2H), 4.60 (d, J=4.4 Hz, 2H), 7.16-7.22 (m, 2H), 7.28-7.37 (m, 2H), 8.69 (t, J=4.4 Hz, 1H).

$^{13}$C-NMR (125 MHz, DMSO-d$_6$): δ=14.2, 46.7 (d, $^3J_{C,F}$=3.9 Hz), 61.8, 111.1, 115.3 (d, $^2J_{C,F}$=21.1 Hz), 124.5 (d, $^4J_{C,F}$=3.4 Hz), 125.8 (d, $^2J_{C,F}$=14.6 Hz), 129.4 (d, $^3H_{C,F}$=8.1 Hz), 129.8 (d, $^3J_{C,F}$=4.3 Hz), 159.4, 159.9 (d, $^1J_{C,F}$=245 Hz).

HRMS: calc. for C$_{11}$H$_{12}$ClFN$_2$O$_2$ 258.0571; found 258.0571.

LC/MS (Method 2): R$_t$=2.21 min; MS (ESIpos): m/z=259 [M+H]$^+$.

Example 3A

Ethyl 1-(2-fluorobenzyl)-1H-imidazo[2,1-c][1,2,4]triazole-3-carboxylate

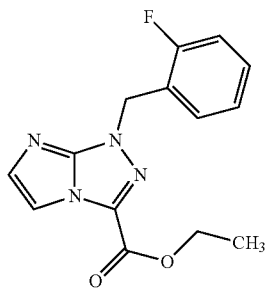

Ethyl (2Z)-chloro[(2-fluorobenzyl)hydrazono]acetate (750 mg, 2.90 mmol) from example 2A, 2-allylthio-1H-imidazole [U.S. Pat. No. 3,574,593; Chem. Abstr. 75, 49078] (1.20 g, 7.25 mmol) and triethylamine (293 mg, 2.90 mmol) are dissolved in dioxane (10 ml) and heated under reflux for 4 h. This is followed by dilution with water and extraction with ethyl acetate. The organic phase is dried over sodium sulfate, and the crude product is purified by chromatography on silica gel (eluent: dichloromethane/methanol 50:1). 410 mg (41% of theory) of the desired product are obtained with 84% purity.

$^1$H-NMR (500 MHz, DMSO-d$_6$): δ=1.35 (t, J=7.1 Hz, 3H), 4.41 (q, J=7.1 Hz, 2H), 5.52 (s, 2H), 7.19-7.28 (m, 2H), 7.29 (s, 1H), 7.39-7.46 (m, 2H), 7.52 (s, 1H).

$^{13}$C-NMR (125 MHz, DMSO-d$_6$): δ=14.0, 46.0 (d, $^3J_{C,F}$=3.7 Hz), 62.1, 107.5, 115.6 (d, $^2J_{C,F}$=20.8 Hz), 122.0 (d, $^2J_{C,F}$=14.8 Hz), 124.7 (d, $^4J_{C,F}$=3.7 Hz), 129.0, 130.7 (d, $^3J_{C,F}$=8.1 Hz), 131.0 (d, $^3J_{C,F}$=3.7 Hz), 136.7, 151.0, 156.2, 160.2 (d, $^1J_{C,F}$=247 Hz).

HRMS: calc. for C$_{14}$H$_{13}$FN$_4$O$_2$ 288.1023; found 288.1021.

LC/MS (Method 1): R$_t$=2.16 min; MS (ESIpos): m/z=289 [M+H]$^+$.

Example 4A

Ethyl 1-(2-fluorobenzyl)-1H-[1,2,4]triazolo[3,4-c][1,2,4]triazole-3-carboxylate

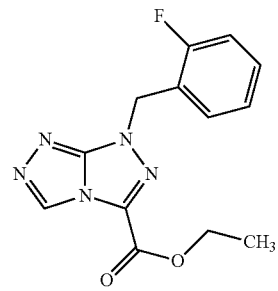

Ethyl(2Z)-chloro[(2-fluorobenzyl)hydrazono]acetate (807 mg, 3.12 mmol) from example 2A, 5-(methylthio)-1H-1,2,4-triazole (359 mg, 3.12 mmol) and triethylamine (316 mg, 3.12 mmol) are dissolved in dioxane (5 ml) and heated under reflux for 6 h. This is followed by dilution with water and extraction with ethyl acetate. The organic phase is dried over sodium sulfate, and the crude product is purified by chromatography on silica gel (eluent: dichloromethane/methanol 50:1). 124 mg (9.5% of theory) of the desired product are obtained with 69% purity.

$^1$H-NMR (500 MHz, DMSO-d$_6$): δ=1.35 (t, J=7.1 Hz, 3H), 4.42 (q, J=7.1 Hz, 2H), 5.53 (s, 2H), 7.21-7.29 (m, 2H), 7.41-7.52 (m, 2H), 8.86 (s, 1H).

$^{13}$C-NMR (125 MHz, DMSO-d$_6$): δ=13.9, 46.7 (d, $^3J_{C,F}$=3.7 Hz), 62.5, 115.6 (d, $^2J_{C,F}$=20.7 Hz), 121.5 (d, $^2J_{C,F}$=14.7 Hz), 124.7 (d, $^4J_{C,F}$=3.5 Hz), 127.8, 130.3, 130.9 (d, $^3J_{C,F}$=8.1 Hz), 131.2 (d, $^3J_{C,F}$=3.4 Hz), 155.4, 158.2, 160.3 (d, $^1J_{C,F}$=247 Hz).

HRMS: calc. for C$_{13}$H$_{12}$FN$_5$O$_2$ 289.0975; found 289.0963.

LC/MS (Method 1): R$_t$=1.95 min; MS (ESIpos): m/z=290 [M+H]$^+$.

EXEMPLARY EMBODIMENTS

Example 1

6-[1-(2-Fluorobenzyl)-1H-imidazo[2,1-c][1,2,4]triazol-3-yl]-1,3,5-triazine-2,4-diamine

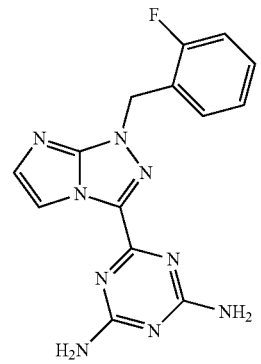

A methanolic sodium methanolate solution (5.4 N, 0.43 ml, 2.30 mmol) is diluted with methanol (3 ml). Biguanidine dihydrochloride (170 mg, 0.98 mmol) is added, and the mixture is stirred at 50° C. for 30 min. Then a solution of ethyl 1-(2-fluorobenzyl)-1H-imidazo[2,1-c][1,2,4]triazole-3-carboxylate (200 mg, 84% pure, 0.58 mmol) from example 3A in methanol (3 ml) is added, and the mixture is heated under reflux for 3 h. It is then diluted with water. The precipitate is filtered off with suction and washed with methanol. 103 mg (55% of theory) of the title compound are obtained.

$^{1}$H-NMR (500 MHz, DMSO-$d_6$): δ=5.48 (s, 2H), 6.96 (br. s, 2H), 7.16 (br. s, 2H), 7.17-7.27 (m, 3H), 7.38-7.46 (m, 2H), 7.86 (s, 1H).

$^{13}$C-NMR (125 MHz, DMSO-$d_6$): δ=45.5 (d, $^{3}J_{C,F}$=3.5 Hz), 109.0, 115.5 (d, $^{2}J_{C,F}$=20.8 Hz), 122.5 (d, $^{2}J_{C,F}$=14.8 Hz), 124.7 (d, $^{4}J_{C,F}$=3.7 Hz), 130.5 (d, $^{3}J_{C,F}$=8.1 Hz), 131.0 (d, $^{3}J_{C,F}$=3.7 Hz), 135.0, 135.6, 151.1, 160.1 (d, $^{1}J_{C,F}$=247 Hz), 161.3, 166.9.

HRMS: calc. for $C_{14}H_{12}FN_9$ 325.1200; found 325.1188.
LC/MS (Method 3): $R_t$=1.46 min; MS (ESIpos): m/z=326 [M+H]$^+$.

Example 2

6-[1-(2-Fluorobenzyl)-1H-[1,2,4]triazolo[3,4-c][1,2,4]triazol-3-yl]-1,3,5-triazine-2,4-diamine

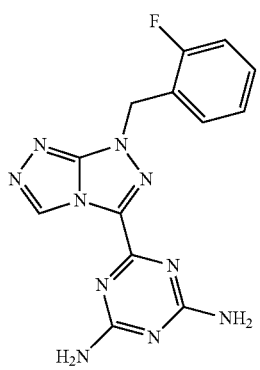

A methanolic sodium methanolate solution (5.4 N, 0.47 ml, 2.54 mmol) is diluted with methanol (3 ml). Biguanidine dihydrochloride (189 mg, 1.08 mmol) is added, and the mixture is stirred at 50° C. for 30 min. Then a solution of ethyl 1-(2-fluorobenzyl)-1H-[1,2,4]-triazolo-[3,4-c][1,2,4]triazole-3-carboxylate (184 mg, 65% pure, 0.36 mmol) from example 4A in methanol (2 ml) is added, and the mixture is heated under reflux for 3 h. It is then diluted with water. The precipitate is filtered off with suction and washed with methanol. 53 mg (39% of theory) of the title compound are obtained.

$^{1}$H-NMR (400 MHz, DMSO-$d_6$): δ=5.49 (s, 2H), 7.04 (br. s, 2H), 7.19 (br. s, 2H), 7.21-7.29 (m, 2H), 7.40-7.51 (m, 2H), 9.00 (s, 1H).

$^{13}$C-NMR (125 MHz, DMSO-$d_6$): δ=46.4 (d, $^{3}J_{C,F}$=3.2 Hz), 115.6 (d, $^{2}J_{C,F}$=20.8 Hz), 122.0 (d, $^{2}J_{C,F}$=14.8 Hz), 124.7 (d, $^{4}J_{C,F}$=3.5 Hz), 130.8 (d, $^{3}J_{C,F}$=8.3 Hz), 131.2 (d, $^{3}J_{C,F}$=3.5 Hz), 131.6, 133.9, 158.2, 160.3 (d, $^{1}J_{C,F}$=247 Hz), 160.5, 166.9.

HRMS: calc. for $C_{13}H_{11}FN_{10}$ 326.1152; found 326.1144.
LC/MS (Method 2): $R_t$=1.17 min; MS (ESIpos): m/z=327 [M+H]$^+$.

B. ASSESSMENT OF THE PHARMACOLOGICAL ACTIVITY

The pharmacological effect of the compounds of the invention can be shown in the following assays:

B-1. Vasorelaxant Effect In Vitro

Rabbits are stunned by a blow to the back of the neck and are exsanguinated. The aorta is removed, freed of adherent tissue, divided into rings 1.5 mm wide and placed singly in 5 ml organ baths with carbogen-gassed Krebs-Henseleit solution of the following composition (in each case mM): NaCl: 119; KCl: 4.8; CaCl$_2$×2H$_2$O: 1; MgSO$_4$×7H$_2$O: 1.4; KH$_2$PO$_4$: 1.2; NaHCO$_3$: 25; glucose: 10, under an initial tension at 37° C. The force of contraction is detected with Statham UC2 cells, amplified and digitized via A/D converters (DAS-1802 HC, Keithley Instruments Munich), and recorded in parallel on chart recorders. A contraction is induced by adding phenylephrine to the bath cumulatively in increasing concentration. After several control cycles, the substance to be investigated is added in each further run in increasing dosage each time, and the level of contraction is compared with the level of contraction achieved in the last preceding run. The concentration necessary to reduce the level of contraction by 50% (IC$_{50}$) is calculated therefrom. The standard application volume is 5 μl, and the DMSO content in the bath solution corresponds to 0.1%.

Exemplary embodiment 1 exhibits an IC$_{50}$ of 6.2 μm in this test.

B-2. Effect on Recombinant Guanylate Cyclase Reporter Cell Line

The cellular effect of the compounds of the invention is determined on a recombinant guanylate cyclase reporter cell line as described in F. Wunder et al., *Anal. Biochem.* 339, 104-112 (2005).

B-3. Determination of Pharmacokinetic Characteristics after Intravenous and Oral Administration The substance to be investigated is administered to animals (e.g. mouse, rat, dog) intravenously as solution; oral administration takes place as solution or suspension by gavage. After administration of the substance, blood is taken from the animals at fixed times. This is heparinized and then plasma is obtained therefrom by centrifugation. The substance is quantified in the plasma analytically by LC/MS-MS. The pharmacokinetic characteristics such as AUC, C$_{max}$, T$_{1/2}$ (half life) and CL (clearance) are calculated from the plasma concentration-time courses ascertained in this way, by means of a validated pharmacokinetic computer program.

B-4. Determination of the Solubility

Reagents Required:
  PBS buffer pH 7.4: weigh 90.00 g of NaCl, analytical grade (e.g. from Merck, Cat. No. 1.06404.1000), 13.61 g of KH$_2$PO$_4$ analytical grade (e.g. from Merck, Cat. No. 1.04873.1000) and 83.35 g of 1 N NaOH (e.g. from Bernd Kraft GmbH, Cat. No. 01030.4000) into a 1 liter graduated flask, make up to the mark with water and stir for about 1 hour;
  acetate buffer pH 4.6: weigh 5.4 g of sodium acetate× 3H$_2$O, analytical grade (e.g. from Merck, Cat. No.

1.06267.0500) into a 100 ml graduated flask, dissolve in 50 ml of water, add 2.4 g of glacial acetic acid, make up to 100 ml with water, check the pH and adjust to pH 4.6 if necessary;

dimethyl sulfoxide (e.g. from Baker, Cat. No. 7157.2500); distilled water.

Preparation of the Calibration Solutions

Preparation of the starting solution for calibration solutions (stock solution): About 0.5 mg of the test substance is weighed accurately into a 2 ml Eppendorf safe-lock tube (from Eppendorf, Cat. No. 0030 120.094), DMSO is added to a concentration of 600 µg/ml (e.g. 0.5 mg of substance+833 µl of DMSO), and the mixture is agitated with a vortexer until dissolution is complete.

Calibration solution 1 (20 µg/ml): 34.4 µl of the stock solution are mixed with 1000 µl of DMSO and homogenized.

Calibration solution 2 (2.5 µg/ml): 100 µl of calibration solution 1 are mixed with 700 µl of DMSO and homogenized.

Preparation of the Sample Solutions:

Sample solution for solubility up to 10 g/l in PBS buffer pH 7.4: About 5 mg of the test substance are weighed accurately into a 2 ml Eppendorf safe-lock tube (from Eppendorf, Cat. No. 0030 120.094), and PBS buffer pH 7.4 is added to a concentration of 5 g/l (e.g. 5 mg of substance+500 µl of PBS buffer pH 7.4).

Sample solution for solubility up to 10 g/l in acetate buffer pH 4.6: About 5 mg of the test substance are weighed accurately into a 2 ml Eppendorf safe-lock tube (from Eppendorf, Cat. No. 0030 120.094), and acetate buffer pH 4.6 is added to a concentration of 5 g/l (e.g. 5 mg of substance+500 µl of acetate buffer pH 4.6).

Sample solution for solubility up to 10 g/l in water: About 5 mg of the test substance are weighed accurately into a 2 ml Eppendorf safe-lock tube (from Eppendorf, Cat. No. 0030 120.094), and water is added to a concentration of 5 g/l (e.g. 5 mg of substance+500 µl of water).

Procedure:

The sample solutions prepared in this way are shaken at 1400 rpm using a controlled-temperature shaker (e.g. Eppendorf thermomixer comfort Cat. No. 5355 000.011 with exchangeable block Cat. No. 5362.000.019) at 20° C. for 24 hours. 180 µl are removed from each of the solutions and transferred into Beckman polyallomer centrifuge tubes (Cat. No. 343621). These solutions are centrifuged at about 223 000×g for 1 hour (e.g. Beckman Optima L-90K ultracentrifuge with type 42.2 Ti rotor at 42 000 rpm). 100 µl of the supernatant are removed from each sample solution and diluted 1:5, 1:100 and 1:1000 with the solvent used in each case (water, PBS buffer 7.4 or acetate buffer pH 4.6). A portion of each dilution is dispensed into a suitable vessel for HPLC analysis.

Analysis:

The samples are analyzed by RP-HPLC. A two-point calibration plot of the test compound in DMSO is used for quantification. The solubility is expressed in mg/l. Analysis sequence: 1) calibration solution 2.5 mg/ml; 2) calibration solution 20 µg/ml; 3) sample solution 1:5; 4) sample solution 1:100; 5) sample solution 1:1000.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; eluent A: water/phosphoric acid pH 2; eluent B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; eluent A: water+5 ml perchloric acid/l; eluent B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

C. EXEMPLARY EMBODIMENTS OF PHARMACEUTICAL COMPOSITIONS

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:

A mixture of compound according to the invention, lactose and starch is granulated with a 5% strength solution (m/m) of the PVP in water. The granules are dried and subsequently mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:

Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

I.V.-Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

L-CH$_2$-M-Q  (I), in which

L is phenyl substituted up to twice by halogen,

M is (d)

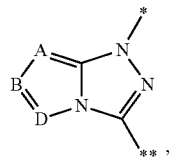
(d)

* is the point of linkage to the —CH$_2$-L group,
** is the point of linkage to the Q group,
A is N,
B and D are each CH, and
Q is an unsaturated 6-membered heterocycle having up to four heteroatoms, which may be substituted up to four times by —NH$_2$, or a salt, an N-oxide, or salt of an N-oxide thereof.

2. 6-[1-(2-Fluorobenzyl)-1H-imidazo[2,1-c][1,2,4]triazol-3-yl]-1,3,5-triazine-2,4-diamine:

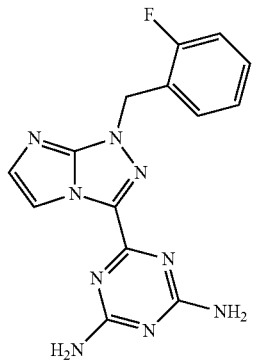

or a salt, an N-oxide, or salt of an N-oxide thereof.

3. 6-[1-(2-Fluorobenzyl)-1H-[1,2,4]triazolo[3,4-c][1,2,4]triazol-3-yl]-1,3,5-triazine-2,4-diamine:

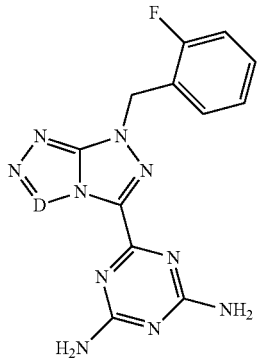

or a salt, an N-oxide, or salt of an N-oxide thereof.

4. A pharmaceutical composition comprising a compound of claim 1, 2, or 3 in combination with an inert, non-toxic pharmaceutically suitable excipient.

5. The pharmaceutical composition of claim 4 further comprising an active ingredient selected from the group consisting of organic nitrates, NO donors, cGMP-PDE inhibitors, agents having antithrombotic activity, agents lowering blood pressure, and agents altering lipid metabolism.

* * * * *